United States Patent [19]
Bonnet et al.

[11] Patent Number: 5,722,996
[45] Date of Patent: Mar. 3, 1998

[54] ACTIVE IMPLANTABLE MEDICAL DEVICE HAVING A CONTROL FUNCTION RESPONSIVE TO AT LEAST ONE PHYSIOLOGICAL PARAMETER

[75] Inventors: Jean-Luc Bonnet, Vanves; Laurence Geroux, Le Plessis Robinson, both of France

[73] Assignee: Ela Medical S.A.

[21] Appl. No.: 674,261

[22] Filed: Sep. 17, 1996

[51] Int. Cl.$^6$ ................................................ A61N 1/365
[52] U.S. Cl. ................................................ 607/17
[58] Field of Search ........................... 607/17, 18, 19, 607/20, 21, 22

[56] References Cited

U.S. PATENT DOCUMENTS

| | | | |
|---|---|---|---|
| 4,867,161 | 9/1989 | Shaldach | 128/419 |
| 5,014,702 | 5/1991 | Alt | 128/419 |
| 5,097,831 | 3/1992 | Lekholm | 607/17 |

FOREIGN PATENT DOCUMENTS

| | | | |
|---|---|---|---|
| 0 249 820 | 12/1987 | European Pat. Off. | A61N 1/365 |
| 0 331 309 | 9/1989 | European Pat. Off. | A61N 1/365 |
| 0 452 732 | 10/1991 | European Pat. Off. | A61N 1/37 |
| WO 92/03182 | 3/1992 | WIPO | A61N 1/365 |

*Primary Examiner*—Scott M. Getzow
*Attorney, Agent, or Firm*—Orrick Herrington & Sutcliffe LLP

[57] ABSTRACT

An active implantable medical device, particularly a cardiac pacemaker, enslaved to at least one physiological parameter. The device is susceptible to function in an enslaved mode by controlling at least one function, particularly that of a cardiac stimulation frequency, based on at least one physiological parameter, and includes at least one effort sensor, measuring a predominantly physiological parameter and delivering an output signal that is a function of the effort developed by a patient bearing the device and at least one activity sensor, especially a sensor having a response time that is more rapid than the effort sensor, for measuring a predominantly physical parameter. The device also includes a selection means, functioning in response to at least one activity and at least one effort signal of each of the sensors, to analyze periodically the relative sequence of successive state changes of the sensors according to predetermined criteria intrinsic to the device, and to select one of the sensors for the enslavement function as a result of this analysis, in a manner to realize, at a given moment, an enslavement mode function respecting most nearly the physiology of the patient corresponding to the activity and effort level of the patient at the given moment.

27 Claims, 5 Drawing Sheets

FIG. 3

| | | SENSOR 2 (EFFORT) | |
| --- | --- | --- | --- |
| Fconsig | REST | EXER | RECUP |
| REST | Fconsig = Fbase | IF<br>Tcapt2 < Tcapt2_max<br>THEN<br>Fconsig = Fcapt2<br>OTHERWISE<br>Fconsig = Fbase | IF<br>Tcapt2 < Tcapt2_max<br>THEN<br>Fconsig = Fcapt2<br>OTHERWISE<br>Fconsig = Fbase |
| EXER | IF<br>Tcapt1 < Tcapt1_max<br>THEN<br>Fconsig = Fcapt1<br>OTHERWISE<br>Fconsig = Fbase | Fconsig = Fcapt2 | Fconsig = Fcapt2 |
| RECUP | IF<br>Tcapt1 < Tcapt1_max<br>THEN<br>Fconsig = Fcapt1<br>OTHERWISE<br>Fconsig = Fbase | Fconsig = Fcapt2 | Fconsig = Fcapt2 |

SENSOR 1 (ACTIVITY)

FIG. 4

| PLATEAU | SENSOR 2 (EFFORT) | | |
|---|---|---|---|
| | REST | EXER | RECUP |
| REST | PLATEAU = 0 | IF Tcapt2 < Tcapt2_max THEN IF PLATEAU = 0 AND Fcapt2 > Fasser THEN PLATEAU = 1 OTHERWISE PLATEAU UNCHANGED OTHERWISE PLATEAU = 0 | PLATEAU = 0 |
| EXER | IF Tcapt1 < Tcapt1_max THEN IF PLATEAU = 0 AND Fcapt1 > Fasser THEN PLATEAU = 1 OTHERWISE PLATEAU UNCHANGED OTHERWISE PLATEAU = 0 | IF PLATEAU = 0 AND Fcapt2 > Fasser, THEN PLATEAU = 1 OTHERWISE PLATEAU UNCHANGED | PLATEAU = 0 |
| RECUP | PLATEAU = 0 | IF PLATEAU = 0 AND Fcapt2 > Fasser, THEN PLATEAU = 1 OTHERWISE PLATEAU UNCHANGED | PLATEAU = 0 |
| SENSOR 1 (ACTIVITY) | | | |

ACTIVE IMPLANTABLE MEDICAL DEVICE HAVING A CONTROL FUNCTION RESPONSIVE TO AT LEAST ONE PHYSIOLOGICAL PARAMETER

FIELD OF THE INVENTION

The present invention is directed to an "active implantable medical device" such as those defined by the Jun. 20, 1990 directive 90/385/EEC of the European Community Council, and more particularly to cardiac pacemakers and/or defibrillators, having a function that is enslaved to, i.e. responsive to, a parameter sensed by a sensor. Although the following description refers mainly to the case of a cardiac pacemaker, the invention also is applicable in a general manner to a great variety of electronic devices having a control function that is responsive to a sensed parameter.

BACKGROUND OF THE INVENTION

Active implanted medical devices are known to adapt their actions, for example, a control function such as the stimulation frequency in the case of a cardiac pacemaker, to the measured or calculated value of a parameter representative of the metabolic needs (cardiac output requirements) of the patient bearing the device.

EP-A-0 089 014 describes the utilization of the measure of the respiratory frequency to vary the instantaneous cardiac stimulation frequency. Multiple parameters, such as minute ventilation, the measure of the oxygen saturation in the blood, the blood temperature, and the acceleration have been acceptably used as parameters of enslavement. As used herein, the terms "enslavement" and "enslaved" mean the control function has a determined result or output that varies as a function of the monitored parameter. The functional relationship may be linear, non-linear, defined by an algorithm or a look-up table, and may be predetermined or self-adjusting.

In the case of cardiac pacemakers, all these enslavement systems compete to increase the stimulation pulse frequency when one detects an increasing activity of the patient, and to decrease the stimulation pulse frequency to a base or minimum frequency in case of a diminution of activity, and particularly during phases of rest of the patient.

Some sensors, such as are described in EP-A-0 493 220, give an adequate representation of metabolic needs of the patient, but present relatively long response times, so that they are not well-suited to vary the stimulation frequency during efforts of short duration. The term "effort" is used to refer to an activity level that is above the rest state, as will be explained. Other sensors, such as that described in FR-A-2 685 642, present a relatively short response time and allow to detect rapidly a change of the patient's activity. These devices are particularly well-adapted to detect the beginning of an effort phase. In this regard, for simplification in the following discussion, an "effort sensor" refers to a sensor measuring a parameter that is a physiological parameter indicative of cardiac output requirements and an "activity sensor" refers to a sensor measuring a parameter also indicative of cardiac output requirements but having a shorter response time than the effort sensor. Further, the effort sensor preferably monitors a parameter that is more physiological than the activity sensor parameter. The latter thus may be referred to as a physical parameter.

It is known in the art to associate information provided by two different types of sensors so as to benefit from the advantages of each of them. Such an association is described in U.S. Pat. No. 5,014,702 and U.S. Pat. No. 5,065,759. U.S. Pat. No. 5,014,702 describes a method where the effort sensor generally serves to confirm information delivered by the activity sensor. The activity sensor primarily determines the stimulation frequency. The effort sensor then confirms or invalidates the presence of or an increase in physical exercise and, in case of confirmation, can vary the stimulation frequency by increasing the stimulation frequency by a predetermined value (e.g., 15 bpm). The reverse case, where the effort sensor first detects exercise which is confirmed or invalidated by the activity sensor, also is described.

U.S. Pat. No. 5,065,759 describes a method where the predominance of the frequency adjustment is given to the effort sensor, the indications of this last sensor being considered following the sensing of the amplitude of variations recorded by the other sensor. Nevertheless, these variations and these amplitudes are determined by comparison to reference curves that are specific to the patient and pre-registered (pre-programmed) in the device.

OBJECTS AND SUMMARY OF THE INVENTION

It is an object of the present invention to overcome the disadvantages associated with these earlier proposed techniques, by applying an active implantable medical device, particularly an improved cardiac pacemaker, enslaved to a parameter that is sensed by an appropriate sensor.

It is another object to provide an improved association of an effort sensor and an activity sensor, more particularly to a reciprocity of respective confirmations of acquired sensor signals, that is to say by "crossed supervision" of each sensor indication by the other sensor.

It is another object to provide an improved adaptive control function of the cardiac stimulation frequency, operated according to at least one of those sensors that will have been chosen at a given moment by the system, and not by a predetermined sensor, taking advantage of the fact that the effort sensor and activity sensor have different response times so as to use better the proper characteristics of each sensor as a function of the stage of evolution of the activity of the patient: beginning of activity, confirmed activity, recovery after an effort, etc.

It is another object to provide an enslaved functioning and management system that is entirely independent of all programmed stabilizing coefficients and reference curves introduced or determined for each patient.

It is another object of the invention to enslave the control function to follow the indications of the first sensor to have detected a beginning of exercise.

It is yet another object of the invention to filter out possible artifacts, and to detect and disregard "gaps" in the information provided by a sensor. (These "gaps" in information, which will be defined more precisely below, can be considered as intermittent declines of the information signal delivered by either one of the effort and activity sensors that do not result from an actual decline of patient activity).

The present invention, therefore, is directed to an active implantable medical device, more particularly to a cardiac pacemaker, having a control function enslaved to at least one physiological parameter in which the measure of the physiological parameter(s) determines in some way at least one operating function of the device, and particularly the cardiac stimulation frequency in the case of the cardiac pacemaker. One such device includes at least one effort sensor, measuring a preponderantly physiological parameter and delivering an output signal that is a function of the effort developed by a patient bearing the device; and at least one activity sensor measuring a preponderantly physical parameter and delivering an output signal that is a function of the patient's effort as determined by the physical parameter, preferably the activity sensor having a faster response time than the effort sensor.

In a preferred embodiment, the invention also includes a selection means, functioning in response to the output signals of each of the activity and effort sensors, to analyze periodically the relative sequence of successive changes of state of the sensors according to predetermined criteria intrinsic to the device, and to select one of the sensors to function (i.e., to use the parameter of the selected sensor as the control parameter of the enslavement function) as a result of this analysis. In this manner, the invention realizes, at any given moment, an enslavement respecting most nearly the physiology of the patient corresponding to his/her activity and effort level at the given moment.

Preferably, each of the activity and effort sensors is susceptible to have at least three distinct state functions of activity detected by the parameter measured by each sensor. These three states correspond respectively to a phase of rest ("REST"), a phase of exercise ("EXER") and a phase of recovery ("RECUP"). For each sensor, one can anticipate that it changes to or will be in (i) the REST state corresponding to the rest phase when the measured parameter is less than a predetermined threshold, (ii) the EXER state corresponding to the exercise phase when the measured parameter is greater than the predetermined threshold and increasing or stable, and (iii) the RECUP state corresponding to the phase of recovery when the measured parameter is greater than the predetermined threshold and strictly decreasing.

The selection means preferably determines and compares the states of the two respective sensors during the same measurement cycle and associates with each possible combination of states a control value to determine the enslaved functioning of the device. In this last case, the invention preferably also includes a control means of crossed indications of sensors, operable to compare the state determined by the output signal of the activity sensor and the state determined by the output signal of the effort sensor and to terminate the enslaved mode of functioning in case of non-concordance. More preferably, the crossed indications control means advantageously terminates the enslaved mode of functioning when the non-concordance is observed to continue either during a time greater than a predetermined duration, or after a predetermined number of repetitions of the comparison step.

In one embodiment, the device in accordance with the present invention has, in addition, means of protection against interruptions of information, to discriminate between on the one hand a decline or end of activity and on the other hand an intermittent decline of the output signal, delivered by either one of the sensors that does not result from a decline of activity. The protection means preferably operates to maintain constant, in case of an intermittent activity decline, the value of the aforementioned control function enslaved to the parameter represented by the sensor output using advantageously a determined, binary state variable. It should be understood, however, that the invention is not limited to a sensor output signal that increases with increasing patient activity or effort.

In one embodiment, the control is the result of a comparison between the value of the aforementioned control function and a control value. In an alternate embodiment, the control is determined relative to the preceding value of the state variable. In yet another embodiment, the control is determined relative to the states of the two sensors.

BRIEF DESCRIPTION OF THE DRAWINGS

Other characteristics and advantages of the present invention will appear to a person of ordinary skill in the art in view of the following detailed description, made with reference to the drawings annexed, in which:

FIGS. 3 and 4 are tables indicating logical actions taken by the device according to the respective sensor states.

DETAILED DESCRIPTION OF THE DRAWINGS

In the detailed description that follows, the example of a cardiac pacemaker enslaved to a physiological parameter is discussed. This application is not, however, restrictive, and the teachings of the invention are directly applicable to other types of active implantable medical devices. Similarly, although the example refers to two sensors only, one can anticipate a more elaborate version having a greater number of sensors, multiplexed or otherwise combined between them, allowing to enslave the functioning of the device to a plurality of different physiological and/or physical parameters. Further, the sensor types described here (namely a minute ventilation sensor for the effort sensor and an acceleration sensor for the activity sensor) are illustrative and not restrictive, and the use of other types of sensors can be envisaged.

It is noted that the operating characteristics, particularly the response times, of these two respective sensor types are different. This allows advantageously to cumulate their advantages when one combines their functioning, as follows: the minute ventilation sensor presents a response time that is relatively long, but delivers a signal that is highly representative of metabolic needs of the patient. On the other hand, the accelerometer sensor has an extremely short response time, but it does not give an indication of the real metabolic needs of the patient.

Figure 1:
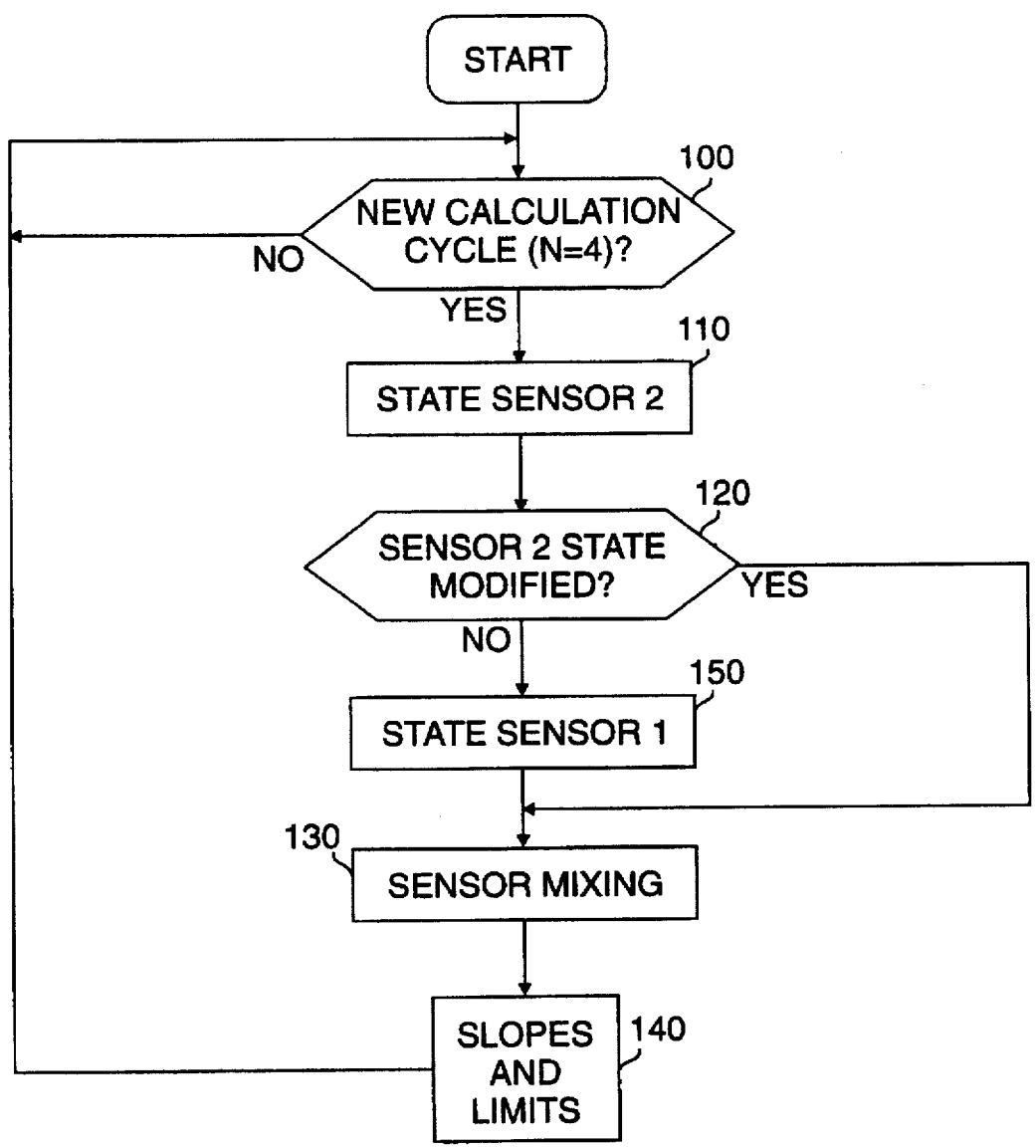
FIG. 1 is a general flow chart of the function of the device in accordance with a preferred embodiment of the invention.

Referring to FIG. 1, the illustrated algorithm allows to calculate a frequency of enslavement (e.g., cardiac stimulation frequency) from two sensors whose information (i.e., the sensor output signals) is regularly measured by the pacemaker, typically every 1.5625 second for the acceleration sensor and each respiratory cycle for the minute ventilation sensor. The measure of these parameters is in itself known, does not form a part of the invention, and this aspect will not be described in detail here. These parameters are transformed into a frequency that one will call hereafter "sensor frequency", or more specifically "frequency MV" for the minute ventilation sensor and "frequency G" for the acceleration sensor. Similarly, in the following discussion, one will call "Sensor 1" the activity sensor, that is to say the sensor allowing to detect rapidly a beginning or an end of activity, but not giving an output signal having a level proportional to the effort (typically an acceleration sensor, designated "G"), and one will call "Sensor 2" the effort sensor, whose response time at the beginning and end of activity is longer than the response time of Sensor 1, but which gives an output signal that is accurately representative of the level of metabolic need of the patient (typically a minute ventilation sensor, designated "MV"). One will note however that the difference in response time between the sensors is inevitably not very important, the minute ventilation being known, for example, as a physiological parameter presenting in the beginning of effort a reasonably rapid response time.

The illustrated general algorithm of FIG. 1 corresponds to a base cycle that is used systematically, for example, every four cardiac cycles. A loop test to determine whether to begin a new cycle is performed at step 100. The routine then examines (step 110) the state of Sensor 2 and tests whether or not the state of Sensor 2 has been modified (step 120).

If there has been a change, the routine determines at step 130, according to predetermined criteria which will be clarified hereunder, the sensor that will control the enslavement. This is followed by an application of slopes and limits at step 140 to avoid too rapid variations of the cardiac frequency (according to algorithms, in themselves known, of management of the increase and decrease of the cardiac signal for an enslaved pacemaker). If there has not been a change, the routine analyzes the state of Sensor 1 to determine if there has been a transition of its state (step 150). The routine then continues with steps 130 and 140 as previously discussed.

Figure 2:
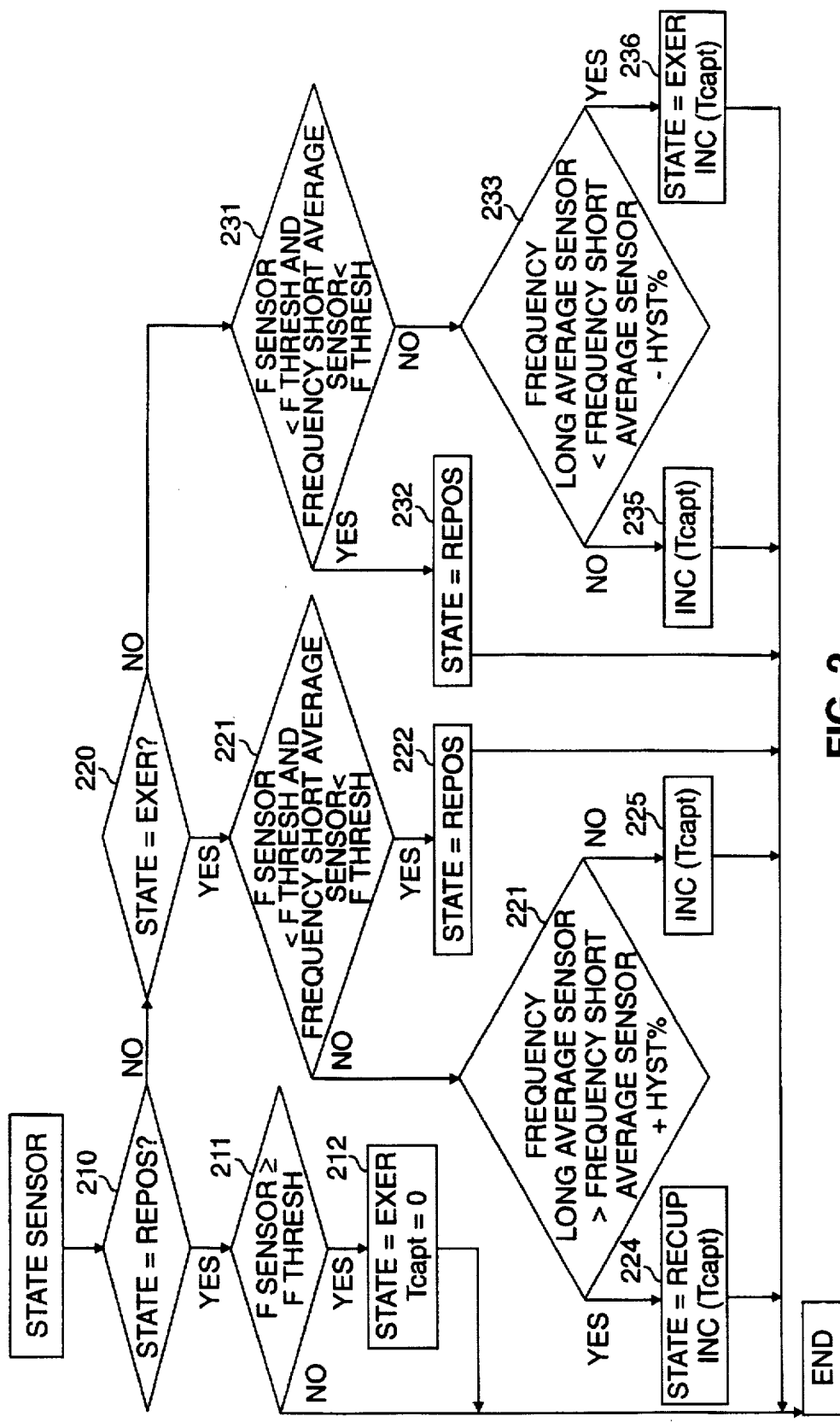
FIG. 2 is a flow chart that details the portion of FIG. 1 relative to the analysis of the state of sensors.

Referring to FIG. 2, the flow chart illustrates the determination of the state of Sensor 2 (step 110 of FIG. 1); it should be understood that this flow chart, with some minor differences, also applies to the case of the determination of the state of Sensor 1 (step 150 of FIG. 1).

For each of the sensors, three different states are defined, as follows: "REST" is defined as when the detected activity is less than a predetermined threshold (said phase "of rest"); "EXER" is defined as when the activity is greater than a predetermined threshold and is increasing or stable (said phase "of exercise"); and "RECUP" is defined as when the activity is greater than the predetermined threshold and is strictly decreasing (said phase "of recovery"). Furthermore, different sensor frequencies are defined, in the same manner for each of the two sensors, as:

"Instantaneous Frequency Sensor" is the sensor frequency determined by the relationship of enslavement (the relationship that links the measure of the output signal delivered by the sensor to the stimulation frequency).

"Fsensor" is the average of the N last values of instantaneous Frequency Sensor (N typically being different for each sensor);

"Frequency Short Average Sensor" is the average of the X last values of Instantaneous Frequency Sensor (X typically being different for each sensor);

"Frequency Long Average Sensor" is the average of the Y last Instantaneous Frequency Sensor values (Y typically being different for each sensor, and Y>X).

"Fthresh" is the frequency equal to the base frequency of the pacemaker, increased by 6% for Sensor 2, and by 12% for Sensor 1 (these values of course being illustrative and not limiting, and preferably being programmable).

One applies then the following rules, as implemented by the routine illustrated in FIG. 2, for Sensor 1 or Sensor 2 as the case may be:

If the sensor is at REST (step 210), then it is determined if Fsensor ≧Fthresh (step 211). If it is, then the sensor state is set to EXER (step 212), and if not, it remains at REST.

If the sensor is at EXER (step 220), then it is determined whether or not Fsensor<Fthresh and Frequency Short Average Sensor<Fthresh. If the conditions are satisfied, then the sensor state is set to REST (step 222). If not, and if Frequency Long Average Sensor ≧Frequency Short Average Sensor+Hyst (step 223) ("Hyst" being an appropriate parameter of hysteresis), then the sensor state is set to RECUP (step 224); otherwise the sensor remains set to EXER.

If the sensor state is set to RECUP, then it is determined whether or not-Fsensor<Fthresh and Frequency Short Average Sensor<Fthresh (step 231). If these conditions are satisfied, then the sensor state is set to REST (step 232). If not, and if Frequency Long Average Sensor<Frequency Short Average Sensor—Hyst (step 233), then the sensor state is set to EXER (step 234); otherwise the sensor remains set to RECUP.

Another parameter that is determined is a time of sensor activity ("Tcapt"), which is updated each time that one updates the state of sensor to the REST state. In this embodiment, Tcapt is a counter of cycles, but it alternately can be a counter of time. Tcapt is equal to zero if the sensor is set to REST. It is incremented (steps 224, 225, 235 and 234), for example, by the number of cardiac cycles since the last update when the sensor is in the EXER and RECUP states. Tcapt is advantageously used to limit the time of enslavement on a sensor that detects an activity that is not confirmed by the other sensor.

For the determination of the state of Sensor 1 (step 150 of FIG. 1), the routine used is the same as that illustrated in FIG. 2, with the sole difference being in steps 221 and 231, where the only test undertaken is to compare Fsensor to Fthresh.

If one returns to the flow chart of FIG. 1, to simplify the functioning, the routine allows only a single sensor to change state during each cycle of calculation. Therefore, it is necessary to define a priority between the two sensors. In the illustrated example, Sensor 2 is the important sensor, that is to say one first tests the state of Sensor 2. If it has not changed state, then one tests the state of Sensor 1; on the other hand, if the state of Sensor 2 has changed, one does not test the state of Sensor 1. This restriction is not indispensable, but it has, however, an advantage to decrease the number of possible transitions from one cycle to the next, and therefore to simplify management of the "sensor mixing" at step 130.

Figure 5:
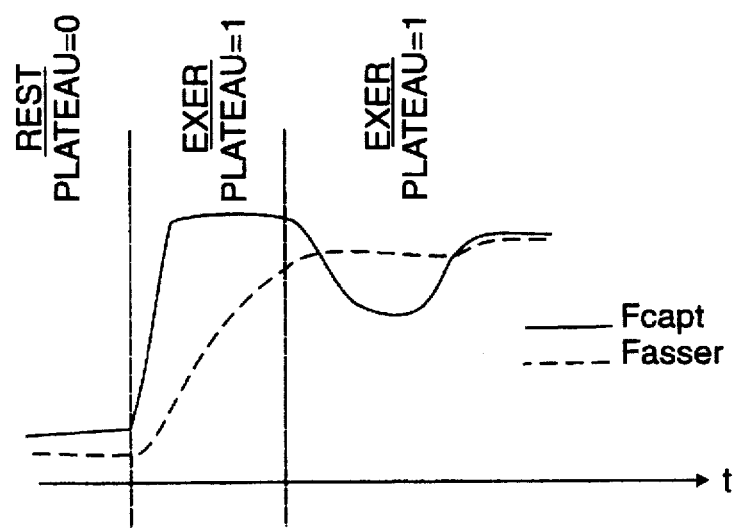
FIGS. 5 to 7 are graphs of rate vs. time which illustrate the behavior of the stimulation frequency according to the invention.
Figure 6:
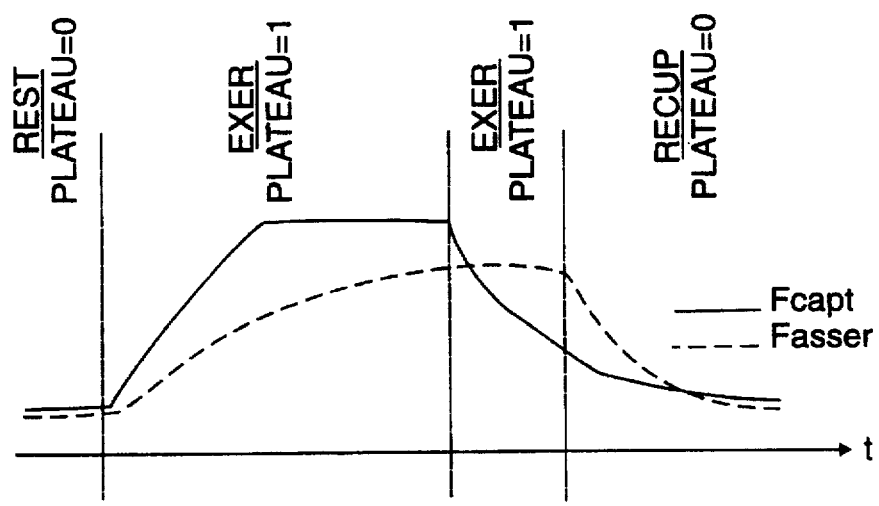
Figure 7:
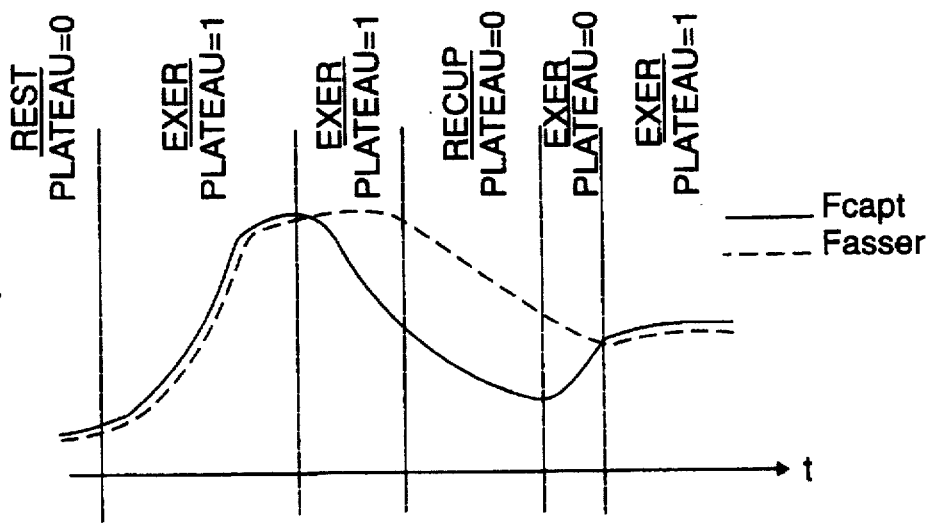

The "sensor mixing" realized at step 130 has for its aim to determine two variables: a control function output frequency "Fconsig," that is the stimulation frequency target that the pacemaker has to reach (Table of FIG. 3), and the variable named "Plateau", that allows the routine to manage gaps of information (Table of FIG. 4). The combination of these two variables, as well as the application of slopes and limits, gives the stimulation frequency of enslavement ("Fasser") to apply to the patient (step 140), that is illustrated in the examples of FIGS. 5 to 7. In the example of the system illustrated, with two sensors and three states for each sensor, there are nine possible combinations that constitute elements of a matrix {3.3} for each of the Tables illustrated in FIGS. 3 and 4. For each combination, one determines a control frequency ("Fconsig"), that is to say a frequency to which the routine will tend to drive the frequency of enslavement. The control frequency Fconsig can take one of three values:

"Fbase": the programmed base frequency;

"Fcapt1": the frequency of enslavement determined from Sensor 1;

"Fcapt2": the frequency of enslavement determined from Sensor 2.

The Table of FIG. 3 provides the detail of the result of the sensor mixing step. It has as a general principle to use as soon as possible the output signal information of Sensor 2. One will notice the symmetry of the first line and the first column. Fconsig takes the value of the frequency of the sensor that has first detected an activity or a recovery during a phase of verification, namely, the period controlled by the parameter Tcapt (with Tcapt<Tcapt__max, Tcapt__max being the maximal predetermined value for each of the sensors), otherwise Fconsig takes the value Fbase.

Based on the principle that Sensor 2 is more representative of metabolic demand of the patient, Fconsig takes the value indicated by this Sensor 2 as soon as it indicates a state in activity (EXER or RECUP) which state is confirmed by Sensor 1. This is illustrated in lines 2 and 3 of columns 2 and 3 in the matrix of possibilities.

Similarly to the determination of Fconsig, the system determines the value of a variable named "Plateau". The object of this variable is to manage the variation of the frequency of enslavement in the presence of a "gap" of output signal information from one of the sensors. One has seen above in the definition of states that EXER and RECUP correspond to an activity, EXER being an increasing activity and RECUP being a decreasing activity. The increase and decrease notion is implicit in conditions given above. Indeed, the principle allowing one to determine if an activity is increasing or decreasing is based on a comparison of the two averages of sensor frequencies, one a short-term average (Frequency Short Average Sensor) and the other a long-term average (Frequency Long Average Sensor).

This principle of the "average crossing" (that has already been described in FR-A-2 671 012 and the corresponding Bonnet U.S. Pat. No. 5,249,572 in the name of the assignee ELA Medical and which is hereby incorporated herein by reference and will not be described in more detail) has for its effect to discriminate between gaps of information and a real end of activity of the patient (passage to REST) or a passage to a lower level of activity (passage to RECUP). One can, therefore, define a gap of information as a diminution of short duration of the value Fsensor, while the state of the sensor remains in EXER. In this case, the frequency of enslavement does not have to be modified and the routine, therefore, applies a "plateau" of frequency, i.e., it maintains the frequency at the same level it was at preceding the determined gap of information.

More precisely, the variable "Plateau" is binary and takes the value '0' when the frequency of enslavement can descend (meaning there is no gap: it concerns an end of effort) and the value '1' when the frequency of enslavement does not have to descend (meaning there is a plateau during a determined gap).

The Table of FIG. 4 sets forth the manner by which the routine determines the value of Plateau, according to the location in the matrix of the system. One will refer to FIG. 4 for the determination, case by case, of the value of Plateau according to states of the different sensors, and the value of this same variable Plateau from the preceding evaluation.

The effective enslavement stimulation frequency Fasser is then calculated from the new value Fconsig and the value of Plateau (step 140, FIG. 1), as follows: If the control frequency Fconsig (given by one of the sensors and Fsensor, following the Table of FIG. 3) is greater than the current enslavement frequency Fasser, the system has detected an activity from one or both sensors. One then increases the frequency of enslavement, if the control frequency is equal to the base frequency, the system has detected a REST, or, alternatively, has invalidated the activity previously detected by one sensor. The frequency of enslavement is then decreased. If the control frequency is greater than the base frequency and less than the current enslavement frequency, the system is found in a case where it has to differentiate between a decline of activity and a gap of information from the sensor used (Sensor 1 or Sensor 2 as the case may be). As Plateau is set to 1 when a frequency plateau is observed (as discussed above), if Plateau=1 the system has not diagnosed decline of activity (the state of the used sensor is EXER) and the frequency of enslavement is not modified. On the other hand, if Plateau=0, the system has diagnosed a decline of activity and the frequency of enslavement is decreased.

One can summarize modes of this function of enslavement by the following rules:

I. If Fasser<Fconsig, then Fasser is increased (with application of slopes and limits previously mentioned).

II. If Fasser>Fconsig, then the routine tests the value of Fconsig. If Fconsig=Fbase (confirming an end of activity), then Fasser descends to Fbase. If Fconsig>Fbase, then the routine tests Plateau. If Plateau=1 (a respiratory gap exists in this example), then Fasser is not modified (plateau); if Plateau=0 (an end or decline of activity), then Fasser descends to Fconsig.

FIGS. 5 to 7 illustrate various experimental results obtained by the present invention. These figures illustrate variations of Fasser under various conditions of the control value Fconsig. FIG. 5 illustrates a REST state, before the detection of an activity by one of the sensors, where Plateau=0. Then, as activity increases, Fasser tends to rejoin the value indicated by Fconsig. Plateau is then set to 1 (passage to the case situated on line 2, column 2 of the matrix of FIG. 4). In the second EXER phase, there is a moment of temporary diminution ("gap of information") of Fconsig, in which case Plateau=1 and the frequency of enslavement preserves the value reached at the moment of the crossing of the frequencies Fconsig and Fasser, that is, when Fconsig falls below Fasser.

FIG. 6 illustrates the behavior of Fasser during a phase of RECUP preceded by a period of EXER. In this case, the frequency of enslavement presents a Plateau before it decreases to the frequency indicated by the sensor.

FIG. 7 illustrates the case of a resumption of activity after a phase of RECUP. In this case, the Plateau variable takes the value 0 (passage to the situated case at line 1, column 2 of the matrix of FIG. 4) so as to allow the frequency of enslavement to rejoin the frequency indicated by the sensor.

The foregoing discussion makes reference to a sensor of a physiological parameter that is the "minute-ventilation" and a physical (non-physiological) parameter such as the acceleration (patient exercise or motion) measured by a sensor, typically a sensor, such as an accelerometer, internal to the device case. Such minute ventilation and accelerometer devices are described, for example, in the U.S. Pat. Nos. 5,299,572, 5,303,702, 5,330,510 and 5,249,572 which are commonly assigned and incorporated herein by reference. But the invention is equally applicable to the use of other physiological parameters, such as those parameters indicated in the introduction of the present description. The invention is also applicable to any physiological or physical parameter that can be sensed or measured, and then used for functions such as an enslavement of active implantable device (and for functions other than enslavement), which can be substituted for the minute—ventilation and/or acceleration, without departing from the scope and framework of the present invention.

The measure of the minute-ventilation is in itself well known. It is described in, for example, the document "Breath-by-Breath Minute Ventilation Measurement Can Provide A Fast Response", by J. L. Bonnet, L. Kramer, Mr. Limousin, EUR. J.C.P.E., 1994, Vol. 4, Abstract Number 329. It also is commercially realized in the device sold under the trade name and model CHORUS RM 7034, manufactured by the ELA Medical, Montrouge, France. The measure of activity also is in itself well known. It is commercially realized in the device sold under the trade name and model OPUS G 4624, manufactured by ELA Medical, Montrouge, France.

Furthermore, the process described herein is preferably implemented using a hardware architecture that includes a microprocessor executing programming instructions from a ROM memory, and having analog and digital logic circuits in themselves known. Such a microprocessor-based structure is, for example, employed in the CHORUS model series of cardiac pacemakers manufactured by ELA Medical. Alternatively, the process may be implemented in an architecture having hardwired discrete and dedicated logic circuits. Although it does not have all of the advantages, including the flexibility, of a realization of the invention in a microprocessor based device, a hardwired structure is nevertheless perfectly foreseeable to be used for the invention, and is equally within the scope and framework of the present invention.

One skilled in the art will appreciate that the present invention can be practiced by other than the described embodiments, which are presented for purposes of illustration and not of limitation.

We claim:

1. An active implantable medical device having a control function that is enslaved to at least one physiological parameter, comprising:

at least one effort sensor, measuring a preponderantly physiological parameter and having an effort output signal corresponding to an effort developed by a patient bearing the device;

at least one activity sensor, measuring a preponderantly physical parameter, and having an activity output signal corresponding to the effort developed by said patient, said activity and effort sensors each having a response time, the activity sensor response time being faster than the effort sensor response time; and selection means, functioning in response to each of the effort and activity sensors, for determining a state of each sensor, identifying a change in state of at least one sensor, periodically analyzing the relative sequence of successive state changes of the effort and activity sensors according to a predetermined criteria intrinsic to the device, and for selecting one of the effort and activity sensors as a function of the result of said periodic analysis, in a manner to realize, at a given instant, an enslavement respecting most nearly the physiology of the patient corresponding to his/her activity and effort level at said given instant.

2. The device of claim 1, in which each of the effort and activity sensors further comprises a state, the state being selectable from among at least three distinct states (REST, EXER, RECUP) determined as a function of the parameter measured by each sensor, the three states corresponding respectively to a phase of rest, a phase of exercise and a phase of recovery.

3. The device of claim 2, in which the sensor state comprises the state (REST) corresponding to the phase of rest in response to the measured parameter being less than a predetermined threshold.

4. The device of claim 2, in which the sensor state comprises the state (EXER) corresponding to the phase of exercise in response to the measured parameter being greater than the predetermined threshold and increasing or stable.

5. The device of claim 2, in which the sensor state comprises the state (RECUP) corresponding to the phase of recovery in response to the measured parameter being greater than the predetermined threshold and strictly decreasing.

6. The device of claim 1, in which the selection means operates to compare the states of the sensors during a given measurement cycle and associates with each possible combination of states a control value (Fconsig) to control the enslaved function of the device.

7. The device of claim 6, further comprising control means of crossed sensor indications, for comparing the state (EXER or RECUP) determined by the output signal of the activity sensor and this same state of activity determined by the output signal of the effort sensor, and terminating the functioning of the device in an enslaved mode in case of non-concordance.

8. The device of claim 7, further comprising a means for determining a time during which said non-concordance persists, wherein the control means of crossed indications operates to terminate the functioning of the device in said enslaved mode in response to said non-concordance persisting for at least a predetermined period, said period being one of a time greater than a predetermined duration, and a predetermined number of repetition of the step of comparison.

9. The device of claim 1, further comprising means of protection against gaps of information, to discriminate between a decline or end of activity and an intermittent decline of one of the sensor output signals that does not result from a decline of activity.

10. The device of claim 9, in which the protection means operates to maintain constant, in a case of a momentary activity decline, a value (Fasser) of the enslaved control function.

11. The device of claim 10, in which the protection means comprises a binary state variable determined by one of:

(i) the result of a comparison between the value (Fasser) and a control value (Fconsig);

(ii) a previous value of the state variable; and (iii) the states of the two sensors.

12. The device of claim 1 wherein the effort sensor comprises a minute ventilation sensor and the effort output signal corresponds to a minute ventilation measurement.

13. The device of claim 12 wherein the activity sensor comprises an acceleration sensor and the activity output signal corresponds to an acceleration measurement of the patient.

14. The device of claim 1 wherein the activity sensor comprises an acceleration sensor and the activity output signal corresponds to an acceleration measurement of the patient.

15. An implantable cardiac pacemaker having an enslaved operating mode in which a cardiac stimulation frequency is determined as a function of at least one physiological parameter of a patient bearing the device in an enslaved operating mode, comprising:

a first sensor, responsive to a physiological parameter of the patient, having an effort output signal corresponding to an effort developed by said patient;

a second sensor, responsive to a physical parameter of the patient, having an activity output signal corresponding to the effort developed by said patient, said first and second sensors each having a response time, the second sensor response time being faster than the first sensor response time;

a signal processor having an input to receive each of the first and second output signals sensors, and operate on said signals to periodically analyze said received effort and activity output signals, determine a state of at least one of said first and second sensors at a given time and determine whether said at least one sensor state has changed from a first state determined at a first time to a second state determined at a second time, and analyze a relative sequence of successive state changes of the first and second sensors according to a predetermined criteria intrinsic to the device; and means for selecting one of the first and second sensors as a function of the result of said periodic analysis, wherein the cardiac stimulation frequency is determined in response to the one selected sensor output signal.

16. The device of claim 15, wherein the signal processor determines for said at least one of the first and second sensors, whether said one sensor is in one of at least a REST state, EXER state, and RECUP state corresponding respectively to a phase of rest, a phase of exercise and a phase of recovery.

17. The device of claim 16 wherein the signal processor determines the state of said first sensor and whether the determined state of said first sensor has changed prior to determining the state of the second sensor.

18. The device of claim 17, wherein the signal processor operates to compare the determined states of the first and second sensors during a given measurement cycle, and said predetermined criteria associates with each possible combination of determined states a control value to control the cardiac stimulation frequency.

19. The device of claim 18 wherein the associated control value is selected from among the group consisting of a base pacing frequency, a first enslaved cardiac stimulation frequency responsive to the effort output signal, and a second enslaved cardiac stimulation frequency responsive to the activity output signal.

20. The device of claim 18, further comprising means for comparing the determined states of the first sensor and the second sensor, determining if said determined states are in non-concordance, and terminating the enslaved operating mode in response to a determined non-concordance.

21. The device of claim 20, further comprising a surveillance duration selected from one of a predetermined time duration, and a predetermined number of comparisons by the comparing means, wherein the comparing means terminates the functioning of the device in said enslaved operating mode in response to a determined non-concordance persisting for said surveillance duration.

22. The device of claim 15, further comprising means for discriminating between a decline or end of activity and an intermittent decline of one of the sensor output signals that does not result from a decline of activity, and, in response to a discriminated momentary activity decline, maintaining constant said enslaved cardiac stimulation frequency.

23. The device of claim 15 wherein the first sensor further comprises a minute ventilation sensor and the second sensor further comprises an acceleration sensor.

24. A method for determining a control function output enslaved to at least a physiological parameter comprising:

(a) monitoring a physiological parameter of a patient corresponding to an effort developed by the patient;

(b) monitoring a physical parameter of said patient corresponding to said effort developed by the patient;

(c) determining a physiological state as a function of the monitored physiological parameter, the physiological state being one of a rest state, an activity state, and a recovery state;

(d) determining a physical state as a function of the monitored physical parameter, the physical state being one of a rest state, an activity state, and a recovery state;

(e) selecting one of said monitored physiological parameter and said monitored physical parameter and determining said control function output as one of a first function of said monitored physiological parameter and a second function of said monitored physical parameter, wherein step (e) further comprises:

(i) determining a first physiological state in response to said monitored physiological parameter sample at a first time;

(ii) determining whether the determined first physiological state is different from a determined physiological state in response to a monitored physiological parameter at a second time prior to said first time;

(iii) in response to said step (e)(ii) not determining a difference in said physiological state, determining a first physical state in response to a first monitored physical parameter at a third time; and (iv) selecting said control function output to be one of the first function and the second function according to a predetermined set of criteria relating the determined effort state and the determined activity state.

25. The method of claim 24 wherein step (e)(iv) further comprises selecting the control function to be one of the first function in response to the monitored physiological parameter at said first time and the second function in response to the monitored physical parameter at said third time.

26. The method of claim 24 wherein steps (c) and (e) are periodically reported having a measurement cycle, and further comprising (e)(v) comparing the determined physiological state and the determined physical state;

(e)(vi) determining whether said compared states are in a non-concordance; and (e)(vii) terminating an operation of the enslaved control function in response to said non-concordance persisting for a predetermined surveillance period.

27. The method of claim 24 further comprising:

(f) identifying a change in the selected one of the monitored physiological parameter and the monitored physical parameter corresponding to a diminution in magnitude, (ii) discriminating an identified diminution in magnitude corresponding to a gap in said monitored parameter from an identified diminution in magnitude corresponding to an end of or decline in said phase of activity, and (iii) maintaining the control function output constant in response to said identified diminution corresponding to a gap.

* * * * *

UNITED STATES PATENT AND TRADEMARK OFFICE
CERTIFICATE OF CORRECTION

PATENT NO.: 5,722,996

DATED: March 3, 1998

INVENTOR(S): Bonnet et al.

It is certified that error appears in the above-identified patent and that said Letters Patent is hereby corrected as shown below:

Column 3, line 56, after "signal;" delete ",";
Column 4, line 67, delete "and,end" and insert --and end--;
Column 7, line 67, delete "if" and insert --If--.

Signed and Sealed this

Fifteenth Day of December, 1998

Attest:

BRUCE LEHMAN

Attesting Officer

Commissioner of Patents and Trademarks